United States Patent [19]

Chen et al.

[11] Patent Number: 6,071,883
[45] Date of Patent: Jun. 6, 2000

[54] FLAVONE ANALOGUES USEFUL AS ANTI-REJECTION AGENTS

[76] Inventors: Huifang Chen, 271 Inglewood Ave., Point-Claire, Quebec, Canada, H9R 2Z3; Feng Li, 506 Boul. St-Jean, Apt. 200, Pointe-Claire, Quebec, Canada, H9R 3J6; Luwei Liu, 30 Eaton Ave., Kirkland, Quebec, Canada, H6H 2S1

[21] Appl. No.: 09/123,313

[22] Filed: Jul. 28, 1998

[51] Int. Cl.[7] .................................................. A61K 31/70
[52] U.S. Cl. .................................................. 514/25; 536/8
[58] Field of Search ................................ 536/8, 9.1, 18.1; 514/25, 53

[56] References Cited

U.S. PATENT DOCUMENTS 5,208,039   5/1993   Poupor et al. ........................... 424/490

OTHER PUBLICATIONS

Li et al Chemical Abstracts No. 110:151, 327c, Apr. 25, 1989.
Kong et al Chemical Abstracts No. 110:151328d, Apr. 25, 1989.
Li et al Chemical Abstracts No. 110:15329e, Apr. 25, 1989.
Chen et al Chemical Abstracts 110:151330y, Apr. 25, 1989.
Li et al Chemical Abstracts No. 114:78637e, Mar. 4, 1991.
Li et al Chemical Abstracts No. 114:220986p, Jun. 10, 1991.
Int. J. Immunopharmac., vol. 16, No. 3, pp. 227–231, 1994, Elsevier Science Ltd. "Immunopharmacology and Toxicology of the Plant Flavonoid Baohuoside–1 in Mice" Li et al.
Int. J. Immonopharmac., vol. 13, Nos.2/3, pp. 129–134, 1991, Pergamon Press plc, "In Vitro Immunopharmacological Profile of the Plant Flavonoid Baohuoside–1" Li et al.
Cancer Letters, 53 (1990) 175–181, Elsevier Scientific Publishers Ireland Ltd. "Effects of the Plant Flavonoid Baohuoside–1 on Cancer Cells in Vitro" Li et al.
Planta Medica 63 (1997) 316–319, "Isolation and Immunomodulatory Effect of Flavonol Glycosides from Epimedium Hunanense" Liang et al.
Acta Pharmaceutica Sinica 1988:23(10):739–748.
English language Abstract of Acta Pharmaceutica Sinica 1988:23(10):739–448.

*Primary Examiner*—Elli Peselev
*Attorney, Agent, or Firm*—Swabey Ogilvy Renault; Kevin P. Murphy

[57] ABSTRACT

Flavone analogues of formula

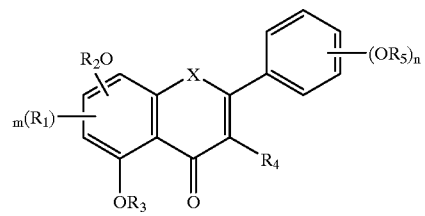

wherein;
X is O or S;
$R_1$ is $C_1$–$C_6$ alkyl or $C_2$–$C_6$ alkenyl;
$R_2$ is H, $C_1$–$C_6$ alkyl or $R_2O$ is a sugar residue;
$R_3$ is H, $C_1$–$C_6$ alkyl or $R_3O$ is a sugar residue;
$R_4$ is H, OH, or a sugar residue;
$R_5$ is H, $C_1$–$C_6$ alkyl, or $R_5O$ is a sugar residue;
m is an integer of 1 or 2; and
n is an integer from 0 to 5,
are useful as anti-rejection agents in organ transplants.

20 Claims, 1 Drawing Sheet

FLAVONE ANALOGUES USEFUL AS ANTI-REJECTION AGENTS

BACKGROUND OF THE INVENTION (a) Field of the Invention

The invention relates to flavone analogues and their use as anti-rejection agents.

(b) Description of Prior Art

Organ transplantation as a treatment modality for patients with end-stage organ disease of the kidney, heart, lung, liver, pancreas and small bowel has achieved impressive results in the past two decades due to greater insight into the immunobiology of graft rejection and better measures for surgical and medical management. A new era in organ transplantation was launched with the successful application of HLA-DR matching and the discovery of cyclosporine A (CsA) CsA-based immunosuppression has substantially improved allograft survival in organ transplantation. Since its clinical use, CsA has become the immunosuppressive drug of choice following organ transplantation and in autoimmune disease (Kahen, *New England J. Med.* 321:1725, 1989). However, the use of CsA is limited because it causes dose-dependent hepatotoxicity and nephrotoxicity (Groth et al., *Transplant Proc.* 25:2681, 1993, and Sorel et al., *Seminars in Nephrology* 17:364, 1997). Although current immunosuppressive protocols have resulted in unprecedented success in solid-organ transplantation, various new agents are being investigated that may provide a greater efficacy and/or a more favorable side-effect profile than those of current regimens.

Over 25 new immunosuppressants are currently under investigation for the treatment or prevention of allograft reactions, and many are already in clinical trials. Each drug has advantages and limitations. CsA and its analogues, for example cyclosporin G and tacrolimus (FK506) are T-cell early activation inhibitors. These drugs block T-cell early activation at the Go/Gl interface and are largely specific for T cells or T-dependent functions initiated through the T-cell receptor complex. In its side effects, FK506 resembles CsA, with regard to nephrotoxicity, neurotoxicity, and hyperglycaemia. CsA also causes hirsutism and gingival hyperplasia (see the aforementioned Groth et al. and Sorel et al.).

Rapamycin (RAPA), a potent immunosuppressant, is currently being investigated in phase III clinical trials for renal transplant rejection. The mechanism of action of RAPA is a blockade of the response of T and B cells to cytokines, thereby preventing cell cycle progression in Gl and consequently cell proliferation. RAPA-associated toxicities include thrombocytopenia, leukopenia, and increases in cholesterol and triglyceride levels.

Mycophenolate mofetil (MMF) is a semi-synthetic derivative of antimetabolic acid, produced by the fungus Penicillium. MMF is a potent, non-competitive, reversible inhibitor of the enzyme inosine monophosphate dehydrogenase. This enzyme catalyzes the conversion of inosine to guanine monophosphate which is required for purine synthesis during cell division. Since activated T and B cells are dependent on de novo purine synthesis. MMF has a mechanism of action distinct from that of CsA, FK506 and PAPA. MMF inhibits the proliferation of T and B lymphocytes, the production of antibodies, and the generation of cytotoxic T lymphocytes. MMF has been shown to prevent acute graft rejection both in experimental and in clinical organ transplantation. The primary side effects of MMF in clinical studies were leukopenia, gastrointestinal problems, and cytomegalovirus disease (Pirsch et al., *Therapeutic Org. Monitoring* 18:358, 1996).

Baohuoside I (3,5,7-trihydroxy-4'-methoxyl-8-prenylflavone-3-O-alpha-L-rhamnopyranoside) a natural flavonoid compound along with other seven novel flavonoids, was first discovered and identified by Feng Li from traditional Chinese herb Epimedium Davidii Franch in 1986 (F. Li et al, *Acta Pharmarceutica Sinica*, 23: 739, 1988).

In 1990, S. Y. Li et al published their investigation results of cytotoxic and cytostatic effects of Baohuoside I on cancer cell lines (*Cancer Letters*, 53: 175, 1990). Later in 1991 they published their results of Baohuoside I for immunpharmacological properties in vitro (*Int. J. Immunopharmac.*, 13: 129, 1991). In 1994, they indicated that Baohuoside I did not significantly prolong survival of cardia grafts and did not potentiate the effects of the standard anti-rejection agent, cyclosporine (*Int. J. Immunopharmac.*, 16: 227, 1994). They further indicated in the same article that the immunosuppressive properties of Baohuoside I are confined to antibody-mediated systems. In the patent of JP91/35790, S. Y. Li et al also indicated that Baohuoside-I does not delay heart allograft rejection.

There remains a need for improved anti-rejection agents, and especially such agents which do not suffer from the disadvantages associated with the prior art agents.

SUMMARY OF THE INVENTION

One aim of the present invention is to provide compounds which are useful as anti-rejection agents.

A further aim of the present invention is to provide anti-rejection agents which exhibit low toxicity.

In accordance with the present invention, it has been found that compounds of formula (X):

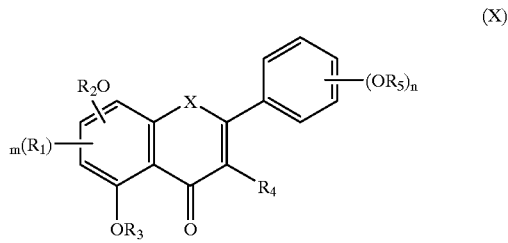

wherein;

X is O or S;

$R_1$ is $C_1$–$C_6$ alkyl or $C_2$–$C_6$ alkenyl;

$R_2$ is H, $C_1$–$C_6$ alkyl or $R_2O$ is a sugar residue;

$R_3$ is H, $C_1$–$C_6$ alkyl or $R_3O$ is a sugar residue;

$R_4$ is H, OH, or a sugar residue;

$R_5$ is H, $C_1$–$C_6$ alkyl, or $OR_5$ is a sugar residue;

m is an integer of 1 or 2; and n is an integer from 0 to 5, are useful as anti-rejection agents in organ transplantations.

The compound (X) may be employed in association with conventional pharmaceutical carriers and excipients or with nutritional products, typically as an injection solution, oral solution or in capsule form for oral administration.

The compounds of formula (X) include novel compounds and the known plant flavonoid known as baohuoside I and which has the chemical name 3,5,7-trihydroxy-4'-methoxy-8-prenylflavone-3-O-2-α-L-rhamnopyraside; the novel compounds may be considered analogs of baohuoside I.

Thus is one aspect of the invention there is provided a method for preventing or suppressing graft rejection consequent from an organ transplant which comprises administering a compound of formula (X) to an animal patient in need of graft rejection prevention.

In another aspect of the invention there is provided compounds of formula (X), with the exception of baohuoside I, as novel compounds.

In still another aspect of the invention there is provided a pharmaceutical composition comprising a therapeutically effective amount of a novel compound of formula (X) in association with a pharmaceutically acceptable carrier.

In still another aspect of the invention there is provided a nutritional composition comprising a therapeutically effective amount of a compound of formula (X) in association with at least one nutritional product.

In still another aspect of the invention there is provided an anti-rejection pharmaceutical composition for use in conjunction with organ transplants comprising an acceptable, anti-rejection amount of a compound of formula (X), in association with a pharmaceutically acceptable carrier.

Still further the invention relates to the use of the compounds of formula (X) in conjunction with organ transplants to prevent graft rejection consequent from an organ transplant.

Still further the invention relates to the use of the compounds of formula (X) in the manufacture of a medicament for preventing allograft rejections consequent upon organ transplants.

In yet another aspect of the invention there is provided in a surgical method in which an animal patient in need, receives an organ transplant to replace a defective organ, and a drug is administered to the patient to prevent or suppress rejection of the organ transplant by the patient, the improvement wherein the drug comprises a compound of formula (X) as defined above.

Thus in particular embodiments the invention provides Baohuoside I and its analogues for use in organ transplantation.

DESCRIPTION OF PREFERRED EMBODIMENTS

In especially preferred embodiments of the invention the compounds (X) are flavonoids, of a sub class designated (XI) of the compounds (X) having the following values:

X is O;

$R_1$ is $C_2$–$C_6$ alkenyl, preferably prenyl;

$R_4$ is a sugar residue;

m is 1, n is 1, $R_2$, $R_3$ and $R_5$ are as described above.

In an especially preferred embodiment $R_4$ is the only sugar residue, and in particular is rhamnopyranosyl.

The alkyl and alkenyl radicals herein may be straight chain or branched chain radicals.

Sugar residues as referred to herein, means the radicals derived by removing a hydrogen atom from a hydroxyl of a sugar. Most preferably, the sugars are monosaccharides which may be open chain or cyclic; and in particular have 5, 6, 7 or 8 carbon atoms, and are pentoses or hexoses. Typically the cyclic sugars have 5 or 6 ring atoms one of which is an oxygen atom.

The preferred compound of formula (X) is the plant flavonoid baohuoside I of formula (XII):

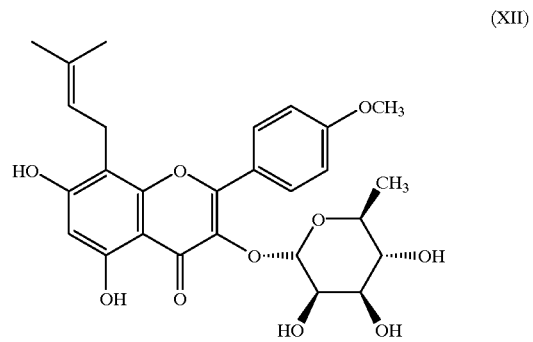

(XII)

Baohuoside I may be isolated from species of Epimedium, for example, *Epimedium davidii* which plant is employed as a herbal remedy known as yinyanghuo in the ancient Chinese pharmacopoeia, or may be produced by a synthetic route.

In a typical extraction procedure, dried whole plants of *Epimedium davidii* are extracted with 95% ethanol. The extract is separated on a medium pressure ligned chromatography column and purified, for example, chromatographically on a Sephadex LH-20 column (Sephadex is a trademark of Pharmacia Fine Chemical for macroscopie beads derived from polysaccharide dextran). The initial extract contains eight prenylflavones including baohuoside I.

A synthetic route for producing Baohuoside I is illustrated below:

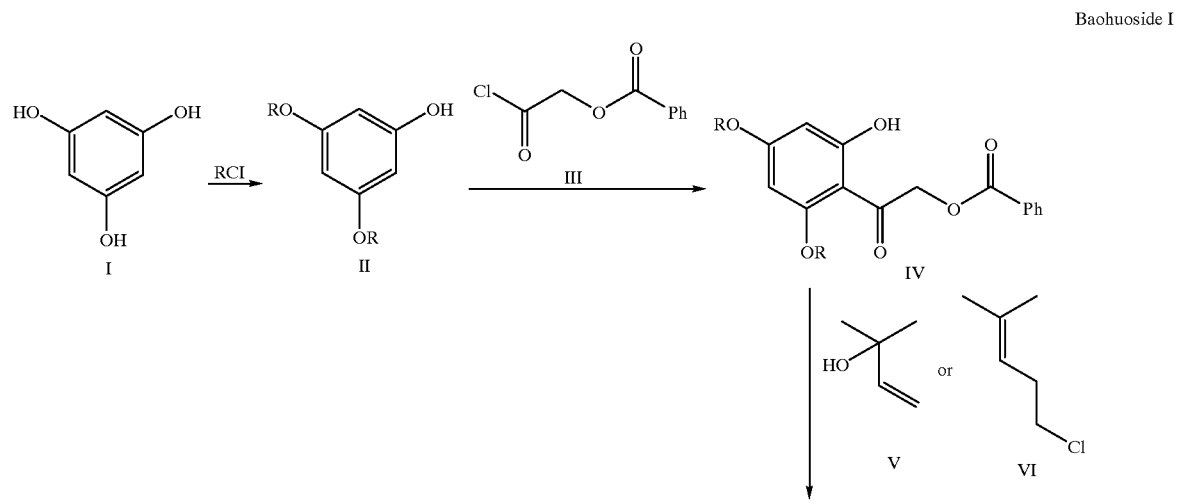

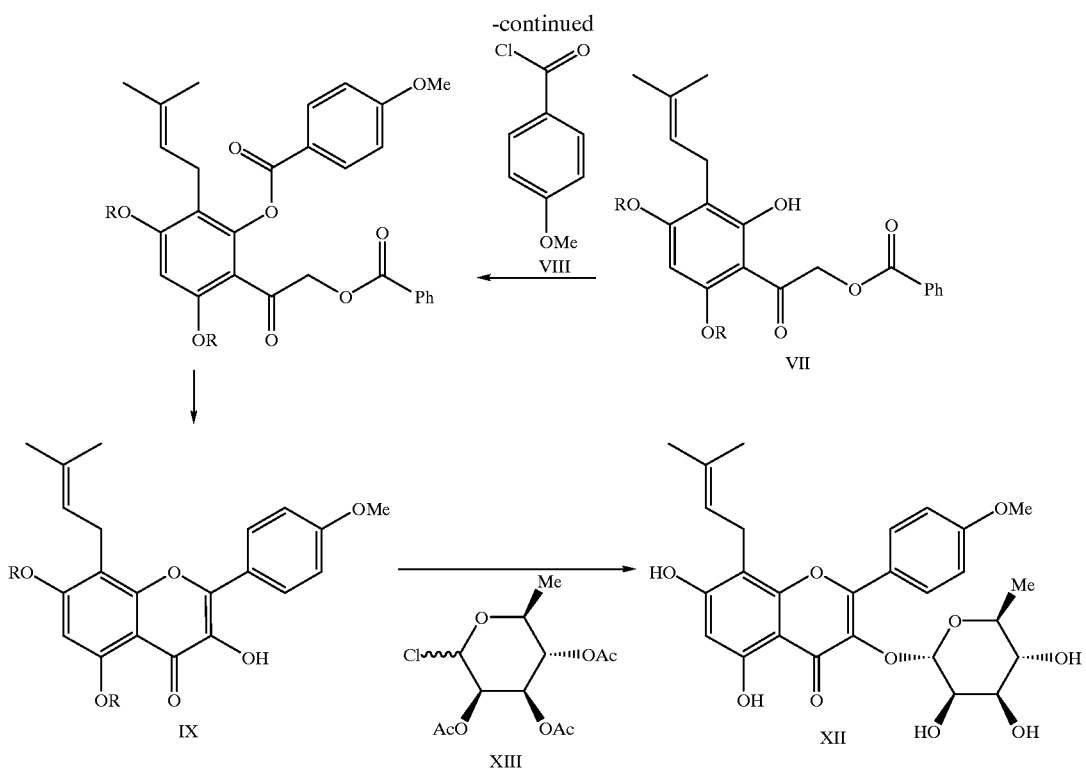

In the above synthetic route R represents a protective group on phenolic hydroxyl, Ph represents phenyl and Me represents methyl.

In the above synthetic pathway 2,4,6-trihydroxybenzene (I) is first selectively protected to give 3,5-protected dihydroxyiphenol (II) using an appropriate protection reagent. The protecting groups could be, for example, ethers such as silyl ether or alkyl ether etc; or esters such as alkyl ester or benzyl ester etc. A Friedel-Crafts reaction on the protected phenol with an alpha-substituted acetyl halide (III) or acetyl anhydride gives the phenone intermediate (V). This ketone intermediate then reacts with 2-methylbut-3-en-2-ol (V) in the presence of a Lewis Acid such as $Bcl_3$, $AlCl_3$ etc or with 4-methylpent-3-enyl chloride (VI) to give the corresponding isopentenylphenone intermediate (VII). The intermediate (VII) then reacts with 4-methoxybenzoyl chloride (bromide or anhydride) to give, after cyclization and deprotection, the corresponding flavonol (IX). The flavonol (IX) then reacts with chloro- or bromo- triacetyl-L-rhamnose (XIII) to give, after deprotection, Baohuoside I (XII).

The synthesis of the analogues of Baohuoside I follows a similar synthetic pathway with similar raw materials which have the substituents identified in formula (X). For example, for 3,5,6-trihydroxy-4'-methoxy-8-isoprenyl-flavon-3-O-alpha-L-rhamnopyranoside, the starting material should be 2,4,5-trihydroxybenzene.

In general the compounds of formula (X) including baohuoside I may be synthesized employing the synthetic pathway below:

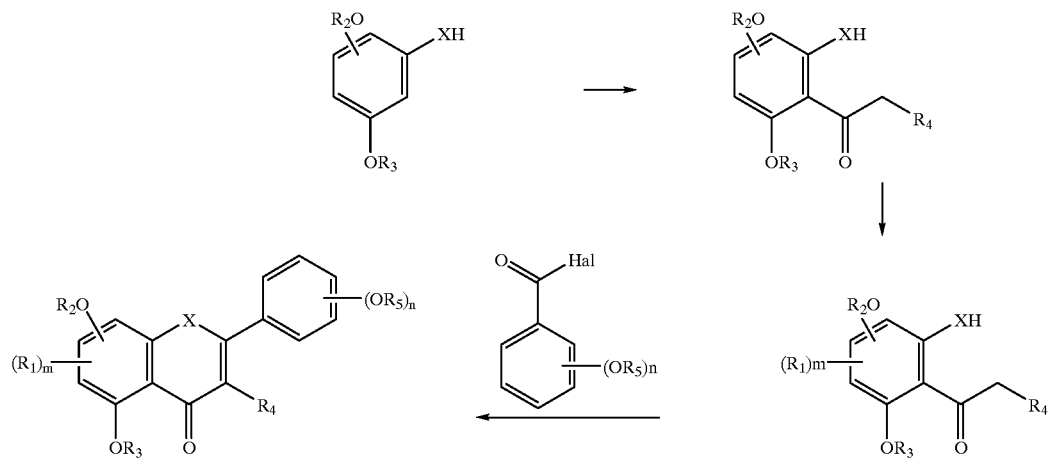

The compound (X) may be employed in association with conventional pharmaceutical carriers and excipients, typically as an injection solution, oral solution or in capsule form for oral administration.

The compound (X) may similarly be employed in association with a nutritional product, for example, a foodstuff as a nutritional formulation for treating an animal patient subjected to an organ transplantation.

EXAMPLE I

Baohuoside-I

Figure 1:
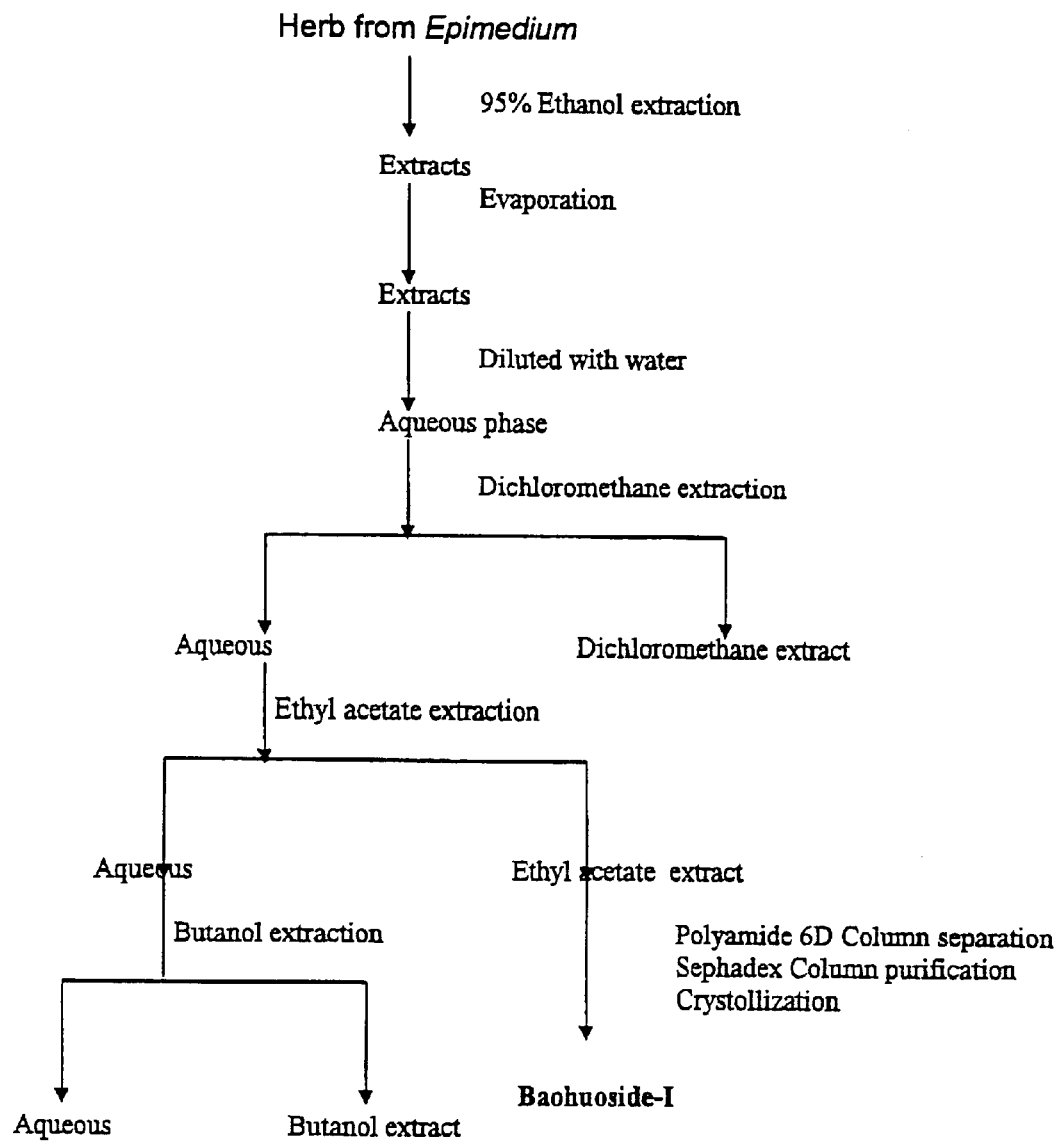
FIG. 1 is a flow sheet illustrating a specific process for extracting Baohuoside I from a species of Epimedium.

Baohuoside I was isolated from *Epimedium davidii*.

Dried whole pants of Epimedium Davidii were extracted with 95% ethanol. After evaporation of ethanol, the extract was diluted with water, and separated with dichloromethane, ethyl acetate and butanol into 3 parts by liquid-liquid extraction. These extracts were dried with sodium sulfate, then solvents were evaporated through a vacuum evaporator. The extracts of ethyl acetate were further separated by preparative medium pressure liquid chromatography on a polyamide 6D (from Merck, Germany) column using chloroform and methanol as a gradient elution system. 22 fractions were collected, each fraction was purified chromatographically on a Sephadex LH-20 (from Pharmacia, Sephadex is a Trade-mark of Pharmacia Fine Chemical, and is derived from polysaccharide dextran) column using methanol as elution solvent. After purification fraction 17 was crystallized in methanol and was identified with MS (Mass Spectrometer), NMR (Nuclear Magnetic Resonance), UV (Ultraviolet Spectroscopy) and IR (Infrared Spectroscopy) and named as Baohuoside-I by Feng Li (F. Li and Y. L. Liu, Acta Pharmaceutica Sinica, 23: 739 1988).

Baohuoside I was similarly isolated, following the same procedure from a species of Epimedium known as Chinese herb "Yinganghuo".

Heart allografts were carried out on mice, and baohuoside I isolated from Epimedium davidii was administrered interperitoneally for 14 days from day 1 after the heart transplant; different groups of mice were administered different dosages of baohuoside I and a control group received no baohuoside I.

The preliminary results shown in Table I below indicate that baohuoside I significantly prolongs mouse heart allograft survival (p=0.001). This result would have been unexpected in the light of the aforementioned 1994 Li et al. publication, and JP91/35790 in which it was demonstrated that baohuoside I did not significantly prolong survival of cardiac grafts, did not delay heart allograft rejections and did not show synergy with CsA in a mice cardiac allograft model.

TABLE 1

Prolongation of cardiac allograft survival treated with baohuoside I in mice (BALB/c to C57BL/10 combination)

| Baohuoside I[a] (mg/kg) | Survival[b] (days) | MST ± SD (days) | P[c] |
|---|---|---|---|
| Controls | 6,6,6,7,7 | 6.1 ± 0.5 | |
| 8 | 8,8,9,9 | 8.5 ± 6.6 | 0.001 |

TABLE 1-continued

Prolongation of cardiac allograft survival treated with baohuoside I in mice (BALB/c to C57BL/10 combination)

| Baohuoside I[a] (mg/kg) | Survival[b] (days) | MST ± SD (days) | P[c] |
|---|---|---|---|
| 16 | 8,8,8,9 | 8.3 ± 0.5 | 0.001 |
| 32 | 10,14,15 | 13.0 ± 2.6 | 0.001 |

[a]Baohuoside I was administered intraperitoneally for 14 days from day 1 after transplanation.
[b]The time of rejection was defined as the last day of palpable cardiac contraction, and was confirmed histologically after laparotomy.
[c]Treated groups were compared with naive controls.

Assessment of the mice for appearance, behavior, biochemistry, haematology and histology revealed no side effects, and no toxic effects at the dosages used previously by S. Y. Li et al. Even in the use of 32 mg/kg/day for 14 days intraperitoneally, no toxic effects were observed.

EXAMPLE II

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended Aclaims.

What is claimed is:

1. A method for preventing or suppressing allograft rejection consequent from an allograft organ transplant which comprises administering to a recipient in need of a graft rejection prevention or suppression, after said allograft organ transplant, a therapeutically effective amount of a compound of formula (X):

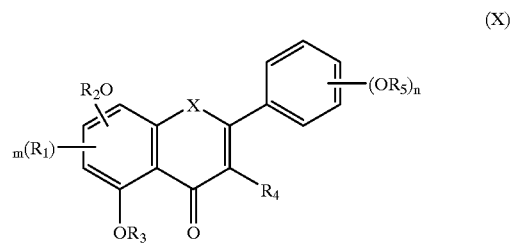

wherein;

X is O;

$R_1$ is $C_2$–$C_6$ alkenyl;

$R_2$ is H or $C_1$–$C_6$ alkyl;

$R_3$ is H or $C_1$–$C_6$ alkyl;

$R_4$ is a monosaccharide residue;

$R_5$ is H or alkyl;

m is an integer of 1 or 2; and n is an integer from 0 to 5.

2. A method according to claim 1 wherein $R_1$ is prenyl, m is 1 and n is 1.

3. A method according to claim 2 wherein $R_4$ is rhamnopyranosyl.

4. A method according to claim 1 wherein said compound of formula (X) is baohuoside I of formula (XII):

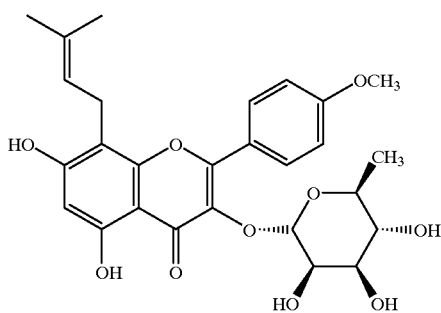

(XII)

5. In a surgical method in which a recipient in need, receives an allograft organ transplant to replace a defective organ, and a therapeutically effective amount of a drug is administered to the recipient, after said allograft organ transplant, to prevent or suppress rejection of the organ transplant by said patient, the improvement wherein said drug comprises a compound of formula (X):

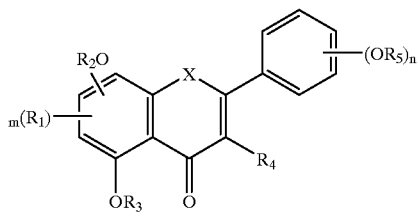

(X)

wherein;
X is O;
$R_1$ is $C_2$–$C_6$ alkenyl;
$R_2$ is H or $C_1$–$C_6$ alkyl;
$R_3$ is H or $C_1$–$C_6$ alkyl;
$R_4$ is a monosaccharide residue;
$R_5$ is H or $C_1$–$C_6$ alkyl;
m is an integer of 1 or 2; and
n is an integer from 0 to 5.

6. The improvement of claim 5 wherein $R_1$ is prenyl, $R_4$ is rhamnopyranosyl, m is 1 and n is 1.

7. The improvement of claim 5 wherein said compound of formula (X) is baohuoside I of formula (XII):

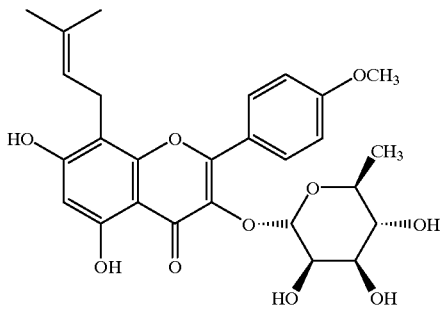

(XII)

8. A method according to claim 2, wherein $R_5$ is H.
9. A method according to claim 3, wherein $R_5$ is H.
10. A method according to claim 2, wherein $R_5$ is methyl.
11. The improvement of claim 5, wherein R is prenyl, m is 1 and n is 1.
12. The improvement of claim 11, wherein $R_5$ is H.
13. The improvement of claim 11, wherein $R_5$ is methyl.
14. The improvement of claim 6, wherein $R_5$ is H.
15. A method according to claim 1, wherein $R_4$ is a pentose or hexose.
16. A method according to claim 2, wherein $R_4$ is a pentose or hexose.
17. The improvement of claim 5, wherein $R_4$ is a pentose or hexose.
18. The improvement of claim 11 wherein $R_4$ is a pentose or hexose.
19. The improvement of claim 12, wherein $R_4$ is a pentose or hexose.
20. The improvement of claim 13, wherein $R_4$ is a pentose or hexose.

* * * * *